(12) United States Patent
Elder et al.

(10) Patent No.: US 10,413,488 B2
(45) Date of Patent: Sep. 17, 2019

(54) AEROSOL OIL FOAM COMPOSITIONS COMPRISING A TRIGLYCERIDE-BASED OIL AND SURFACTANT

(71) Applicant: L'OREAL, Paris (FR)

(72) Inventors: Allison Elder, North Adams, MA (US); Tsung-Hui Marisal Mou, Towaco, NJ (US); Carol Elmasry, South Amboy, NJ (US); Angelike A. Galdi, Westfield, NJ (US); David Chan, Edison, NJ (US); Lisa Yarhyna Lema, Linden, NJ (US)

(73) Assignee: L'OREAL, Paris (FR)

( * ) Notice: Subject to any disclaimer, the term of this patent is extended or adjusted under 35 U.S.C. 154(b) by 79 days.

(21) Appl. No.: 14/957,344

(22) Filed: Dec. 2, 2015

(65) Prior Publication Data
US 2017/0156995 A1 Jun. 8, 2017

(51) Int. Cl.
*C11D 17/00* (2006.01)
*A61K 8/04* (2006.01)
*A61K 8/92* (2006.01)
*A61Q 5/02* (2006.01)
*A61Q 19/10* (2006.01)
*A61K 8/37* (2006.01)

(52) U.S. Cl.
CPC .............. *A61K 8/046* (2013.01); *A61K 8/375* (2013.01); *A61K 8/92* (2013.01); *A61K 8/922* (2013.01); *A61Q 5/02* (2013.01); *A61Q 19/10* (2013.01); *A61K 2800/30* (2013.01); *A61K 2800/31* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 4,808,388 A * | 2/1989 | Beutler | A61K 8/046 424/47 |
| 5,500,211 A | 3/1996 | George et al. | |
| 5,663,154 A * | 9/1997 | Burns | C07H 19/16 514/45 |
| 8,454,942 B1 | 6/2013 | Kasai et al. | |
| 2002/0045670 A1 | 4/2002 | Lorant | |
| 2004/0197276 A1 | 10/2004 | Takase et al. | |
| 2008/0031908 A1 | 2/2008 | Aubrun-Sonneville et al. | |
| 2008/0138293 A1 | 6/2008 | Tamarkin et al. | |
| 2009/0226381 A1* | 9/2009 | Maillefer | A61K 8/898 424/47 |
| 2011/0195035 A1* | 8/2011 | Vondruska | A61K 8/37 424/59 |
| 2012/0308492 A1* | 12/2012 | Allef | A61K 8/046 424/59 |
| 2013/0136701 A1 | 5/2013 | Kasai et al. | |
| 2014/0348756 A1* | 11/2014 | Doering | A61Q 15/00 424/43 |

FOREIGN PATENT DOCUMENTS

JP 2011213680 A * 10/2011
WO 2014204008 A1 12/2014

* cited by examiner

*Primary Examiner* — Lorna M Douyon
(74) *Attorney, Agent, or Firm* — McNees Wallace & Nurick LLC

(57) ABSTRACT

An aerosol oil foam composition having at least one triglyceride-based oil and at least one polyglyceryl fatty acid ester surfactant. The polyglyceryl fatty acid ester surfactant includes an alkyl group having at least 10 carbon atoms and having a hydrophile-lipophile balance of between about 8 and about 13. The aerosol oil foam composition is a stable foam that is water rinsable. An aerosol oil-containing foamable composition and a process for cleansing skin, scalp or hair are also disclosed.

21 Claims, No Drawings

AEROSOL OIL FOAM COMPOSITIONS COMPRISING A TRIGLYCERIDE-BASED OIL AND SURFACTANT

FIELD OF THE INVENTION

The present invention generally relates to oil foam compositions that form stable foams and are water rinsable. More particularly, the present invention relates to a rinsable, waterless, or substantially waterless, oil foam composition, preferably in the form of an oil foam, for application onto a keratinous substrate, such as hair, skin or nails.

BACKGROUND OF THE INVENTION

Cleaning the skin is very important for face care. It must be as effective as possible because the fatty residues, such as excess sebum, residues of the cosmetic products which are employed daily, and make-up products, especially the water-resistant "waterproof" products, accumulate in skin folds and at the surface of the skin and can block skin pores and entail the appearance of spots. In addition, compositions bearing UV Filters often have residues that are difficult to remove simply by rinsing. Poor cleaning quality, and in particular poor rinsing, are often responsible, among other causative factors, for a sallow complexion.

A number of major types of products for cleaning the skin are known: lotions and foaming detergent aqueous gels and oils and biphase makeup removers, milks for removing make-up, and foaming creams which are usually soap-based.

The foaming detergent aqueous lotions and gels can have a cleansing action by virtue of the surfactants which can suspend the fatty residues and the pigments of make-up products. They can be effective and pleasant to use because they can foam and they can be easily removed. However, it is difficult to achieve good cleansing/makeup removal with aqueous cleansers without stripping the skin and many of the good cleansing surfactants are too harsh to be used for eye area safety-wise.

Oily compositions are recognized for their effectiveness as a cleaning agent and/or make-up remover. They, in fact, allow lipophilic soiling and make-up to be dissolved very easily, in particular the "waterproof" and transfer-free make-ups which are known to be difficult to remove. These products are effective and well tolerated. They have the disadvantage of being runny and having a difficult application, not imparting a feeling of freshness on application as well as leaving a residue behind, and this is a disadvantage from a cosmetic viewpoint. Typically, anhydrous systems do not foam very well even with the incorporation of a propellant.

The lotions and the foaming detergent aqueous gels have a cleaning action by virtue of the surfactants which place the fatty residues and the pigments of the make-up products in suspension. They are effective and cosmetically pleasant because they foam and because they are easily removed. Insofar as they do not contain any cosmetic oil, they have the disadvantage of making the skin dry owing to their lipid-removing action and they do not remove makeup as well.

Attempts have been made to design cleaning foaming products which are easily rinsable with water, including oils in large quantities so as to optimize the cleaning of the skin and to hydrate and nourish the latter while avoiding any phenomenon of drying out and of irritation. Oils that produce a foam can be obtained by pressurization of oil with a propellant and packaging as an aerosol. The problem is to obtain foams that are fine, while presenting sufficient stability and rinsability.

Foams are complex dispersion systems which do not form under all circumstances. It is known to be very difficult to produce foams which are homogenous, stable, and which can provide a shelf-stable composition. One of the primary disadvantages associated with the use of foams is their foam stability. In order for the foam to perform satisfactorily, the actives finely dispersed therein must be satisfactorily distributed over the target surface. This in turn requires that the foam be sufficiently stable upon release from its container to allow for adequate coating over the target substrate. These foaming problems are further exacerbated by the fact that oils themselves are known to collapse foams.

It is desirable in the art to provide a foam-stable composition that can be readily rinsed with water and provide the consumer with a clean skin feel and no greasy residue after rinsing.

BRIEF SUMMARY OF THE INVENTION

In an exemplary embodiment, an aerosol oil foam composition having at least one triglyceride-based oil and at least one polyglyceryl fatty acid ester surfactant. The polyglyceryl fatty acid ester surfactant includes an alkyl group having at least 10 carbon atoms and has a hydrophile-lipophile balance of between about 8 and about 13. The aerosol oil foam composition is a stable foam that is water rinsable.

In another exemplary embodiment, a process for cleansing skin, scalp or hair. The process includes applying to the skin, scalp or hair a composition comprising an aerosol oil foam composition having at least one triglyceride-based oil and at least one polyglyceryl fatty acid ester surfactant. The polyglyceryl fatty acid ester surfactant includes an alkyl group having at least 10 carbon atoms and has a hydrophile-lipophile balance of between about 8 and about 13. The aerosol oil foam composition is a stable foam that is water rinsable. The method further includes rinsing with the skin, scalp or hair with water.

In another exemplary embodiment, an aerosol oil-containing foamable composition having (a) at least one triglyceride-based oil, (b) at least one polyglyceryl fatty acid ester surfactant, the polyglyceryl fatty acid ester surfactant comprising an alkyl group having at least 10 carbon atoms and having a hydrophile-lipophile balance of between about 8 and about 13; and (d) a propellant. The aerosol oil-containing foamable composition forms a stable foam that is water rinsable.

In another exemplary embodiment, a method for preparing the composition is provided involving mixing the above-disclosed ingredients to form the composition.

The present invention is also directed to a method for cosmetic treatment of keratinous tissues by applying the above-disclosed composition onto a surface of the keratinous tissue.

Also disclosed herein is the cosmetic use of the composition as defined above, as cleansing and/or make-up-removing products for keratinous materials.

The compositions of the invention preferably constitute rinsable foaming cleansing compositions, which may be used in the field of cleansing of the skin, the hair or other keratinous tissue.

Further disclosed herein is a cosmetic method for cleansing the soiling residues of a human keratinous material, comprising applying the oil foam composition with the soiling residues, and removing the foam and the soiling residues by rinsing with water.

Other features and advantages of the present invention will be apparent from the following more detailed description of the preferred embodiment which illustrates, by way of example, the principles of the invention.

DETAILED DESCRIPTION OF THE INVENTION

All numbers expressing quantities of ingredients and/or reaction conditions are to be understood as being modified in all instances by the term "about", unless otherwise indicated.

"Keratinous tissue," as used herein, includes, but is not limited to, skin, hair, and nails.

"Homogenous" means having the visual appearance of being substantially uniform throughout, i.e., visually appears as a single phase emulsion and/or dispersion.

The term "waterless", as used herein, means that the composition contains from 0% up to 5%, preferably less than 3%, most preferably less than 1% by weight of water, based on the total weight of the composition.

It has been surprisingly and unexpectedly discovered by the inventors that the use of a triglyceride and an alkylated polyglyceryl surfactant having an HLB between 8-13 in the oil-containing foamable composition includes chemical and physical foam stability and water rinsability. The oily foam composition, once expelled from its canister via a propellant, possesses sufficient stability to enable it to be effectively spread over a target keratinous substrate surface.

The compositions according to the invention are stable, produce a fine, stable foam and have very good rinsability with water. The composition may be, for example, a cleansing and/or makeup-removing product for the skin, the scalp and/or the hair, a scrubbing product and/or an exfoliant product for the skin. In one embodiment, the composition, according to the present invention, constitutes a skin cleansing composition.

The compositions, according to the invention, can be presented, for example, in the form of a cleaning product, make-up remover, of a hydrating product, of a deep-cleanser or of an exfoliating agent, and are used as or are other products of these categories to clean the skin by washing or hydrate the skin by applying to the skin, etc.

One embodiment of the present invention includes a waterless foam composition comprising a triglyceride and an alkylated polyglyceryl surfactant having an HLB between 8-13 with propellant. The concentration of the triglyceride can range from 35% to 90% of the formula by weight and the concentration of the alkylated polyglyceryl can range from 6% to 25% of the formula by weight. In this embodiment, the composition is a cosmetic composition, such as, but not limited to cleansers, makeup remover, body mousse, and/or hair mousse.

Triglyceride-Based Oil

The composition, according to the invention, may comprise at least one triglyceride-based oil. "Triglyceride-based oil", as used herein, includes an oil having an ester derived from glycerol and three fatty acids. The triglyceride-based oil, in one embodiment, is devoid of petroleum based oil.

Suitable triglyceride-based oil include, but are not limited to, the following:

(a) triglyceride oils of animal origin; and
(b) triglyceride oils of plant origin, such as triglycerides consisting of fatty acid esters of glycerol, the fatty acids of which may have varied chain lengths from $C_4$ to $C_{24}$, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppyseed oil, pumpkin oil, marrow oil, blackcurrant oil, evening primrose oil, millet oil, barley oil, walnut oil, quinoa oil, rye oil, safflower oil, candlenut oil, camelia oil, passionflower oil or musk rose oil; shea butter; or caprylic/capric acid triglycerides, for instance, those sold by the company Stéarineries Dubois or those sold under the names Miglyol 810®, 812® and 818® by the company Dynamit Nobel.

Particularly suitable triglyceride-based oils are selected from the group consisting of grapeseed oil, walnut oil, sunflower oil, corn oil, apricot oil, camelia oil, olive oil, avocado oil, and combinations thereof.

The triglyceride-based oil is typically present in the composition in an amount of from about 35% to about 90% by weight, preferably from about 30% to about 70% by weight, and more preferably from about 45% to about 65% by weight, based on the total weight of the composition.

Polyglyceryl Fatty Acid Ester Surfactant

The polyglyceryl fatty acid ester surfactant, according to the present invention, is a polyglyceryl fatty acid ester surfactant comprising an alkyl group having at least 10 carbon atoms and having a hydrophile-lipophile balance of between about 8 and about 13. It has surprisingly and unexpectedly been discovered that the use, in particular, of polyglyceryl fatty acid ester surfactant comprising an alkyl group having at least 10 carbon atoms and having a hydrophile-lipophile balance of between about 8 and about 13 facilitates the formation of stable foams created from oils using a propellant, from both a chemical and physical perspective. More particularly, the use of such a surfactant enables the creation of foam that is rinsable with water, wherein the foam is sufficiently foam stable after being dispensed from its receptacle such that it allows for successful application/coverage over the target keratinous substrate.

Suitable polyglyceryl fatty acid ester surfactants include, but are not limited to, the following:

polyglyceryl-2 laurate, in particular, as sold by TAIYO KAGAKU under the name Sunsoft Q-12D-C;

polyglyceryl-10 trilaurate, in particular, as sold by TAIYO KAGAKU under the name Sunsoft Q-123Y-C;

polyglyceryl-5 laurate, in particular, as sold by TAIYO KAGAKU under the name Sunsoft Q-121E-C;

polyglyceryl-10 dioleate, in particular, as sold by TAIYO KAGAKU under the name Sunsoft Q-172Y-C;

polyglyceryl-6 dicaprate, in particular, as sold by TAIYO KAGAKU under the name Sunsoft Q-102H-C; and polyglyceryl-10 isostearate, in particular, as sold by HIHON SURFACTANT under the name Nikkol Decaglyn 1-IS.

At least one surfactant chosen from polyglyceryl fatty acid esters will typically be present in the composition in an amount of from about 6% to about 25% by weight, preferably from about 7% to about 10% by weight, and more preferably from about 8% to about 10% by weight, based on the total weight of the composition.

Propellants

The compositions of the present invention are added together with at least one propellant in a suitable container. This propellant may represent less than 20% by weight of the base composition and, in particular, may represent from 1% to 10% by weight, for example from 2% to 8% by weight, for example, at least 5% by weight of the propellant plus composition. Suitable propellants for use in the present invention include volatile liquefied propellant gases, such as, for example, dimethyl ether (DME) and/or linear or branched-chain hydrocarbons with two to five carbon atoms, such as, for example, ethane, propane, butane, isobutane, isobutene, pentane and tetrafluoropropene, which can be used alone or in admixture with each other. It may especially be a propane/butane mixture (Liquified Petroleum Gas or LPG) in a weight ratio [propane/butane] ranging from 0.1 to 1, especially of 0.31.

Compressed air, as well as other pressurized gases suitable for cosmetic use may also be employed. Examples thereof include, but are not limited to, air, oxygen, nitrogen, hydrogen, helium, krypton, xenon, radon, argon, nitrous oxide and carbon dioxide.

The pressure of the propellant, and, for example, of said propane/butane mixture, in the aerosol may range from 0.20 to 0.50 MPa, for example, from 0.20 to 0.40, and especially from 0.25 to 0.35 MPa.

In order for the foam to be of acceptable quality, both aesthetically and from an application point of view, the foam should possess a density of from about 0.03 to about 0.15 g/ml, preferably from about 0.04 to about 0.08 g/ml, and more preferably from about 0.04 to about 0.06 g/ml.

Auxiliaries

The composition, according to the invention, may comprise at least one dyestuff chosen especially from pigments, nacres, liposoluble dyes and water-soluble dyes, and mixtures thereof.

The term "pigments" should be understood as meaning white or colored, mineral or organic particles of any shape, which are insoluble in the physiological medium and are intended to color the composition.

The term "nacres" should be understood as meaning iridescent particles of any shape, especially produced by certain molluscs in their shell or else synthesized.

The term "dyes" should be understood as meaning generally organic compounds that are soluble in water or in fatty substances, such as oils.

The pigments, if present, may be white or colored, and mineral and/or organic. Among the mineral pigments that may be mentioned are titanium dioxides, optionally surface-treated, zirconium oxide and cerium oxide, and also zinc oxide, iron oxide (black, yellow or red) or chromium oxide, manganese violet, ultramarine blue, chromium hydrate and ferric blue and metal powders, such as aluminum powder or copper powder.

The dyestuffs may be present in an amount of from about 0.01% to about 30% by weight, such as from about 0.1% to about 20% by weight, such as from about 0.5% to about 15% by weight, and most preferably from about 0.5% to about 5% by weight, relative to the total weight of the composition.

In a known manner, the composition of the invention may also contain, in certain embodiments, adjuvants that are common in cosmetics, such as humectants, preserving agents, antioxidants, complexing agents, solvents, fragrances, bactericides, odor absorbers, vitamins, moisturizers, self-tanning compounds and anti-wrinkle active agents. The amounts of these various adjuvants are those conventionally used in the field under consideration, for example, from 0.01% to 20% of the total weight of the composition.

In one embodiment, the composition, according to the present invention, is devoid of UV Filters.

The composition before expansion in volume can be provided in the suspension, dispersion, solution or gel form.

Needless to say, a person skilled in the art will take care to select this or of these optional additional compound(s), and/or the amount thereof, such that the advantageous properties of the composition, according to the invention, are not, or are not substantially, adversely affected by the envisaged addition.

The composition in the foam form, according to the invention, finds its application in a wide variety of treatments, especially cosmetic treatments, of the skin, the lips and the hair, including the scalp, especially for treating, protecting or caring for the skin, the lips and/or the hair, and/or for making up the skin and/or the lips.

Of course, a person skilled in the art will take care to choose this or these optional additional compounds so that the advantageous properties intrinsically attached to the composition, in accordance with the invention, are not, or not substantially, detrimentally affected by the envisaged addition or additions.

Foam Stability

Compositions, according to the present invention, include a composition that forms a "stable foam". By "stable foam" it is meant that the compositions form a foam that initially has a good aesthetic appearance and maintains a foam structure when formed that is sufficiently stable to enable the foam to be properly spread over the target substrate.

Water Rinsability

The compositions, according to the invention, are water rinsable. As utilized herein "water rinsable" and "water rinsability" includes the property of being able to be easily dispersed into and removed with water or aqueous solutions from keratinous tissue. In addition, by water rinsable, the composition, in certain embodiments, includes the property of cleansing and/or makeup-removal from the skin, the scalp and/or the hair with the application of water or aqueous solutions. In one embodiment, the composition, according to the present disclosure, constitutes a skin cleansing composition.

Method

The composition is prepared by combining the ingredients, including the triglyceride-based oil and polyglyceryl fatty acid ester surfactant, in a vessel and heating, while gently mixing until all solids are dissolved, giving a homogeneous phase. The oil phase component is observed to verify that the components are dispersed and the mixing is continued while heating until fully homogeneous.

The composition, according to the invention, can be packaged in a container, such as an aerosol can, delimiting at least one compartment which comprises the composition, according to the present invention, the container being closed by a closure part. The composition in the foam form may be obtained from a base composition in a distributor. This distributor may be an aerosol containing, besides the base composition, a propellant. The container may be equipped with a means for the dispensing of the product. In particular, the container can be equipped with a pump. The container is preferably used in combination with an applicator comprising at least one application component configured in order to apply the composition to keratinous substances. According to another advantageous embodiment, the applicator comprises an application nozzle.

The following examples are intended to further illustrate the present invention. They are not intended to limit the invention in any way. Unless otherwise indicated, all parts are by weight.

EXAMPLES

The following examples are to illustrate the invention and are non-limiting.

Table 1 shows various composition having a composition having varied oil and surfactants. The ingredients were mixed together in a vessel and heated and dissolved at a temperature between 50° C. and 60° C. The resulting solution was cooled to ambient temperature to form the foamable composition. The composition was loaded into an aerosol can and the can was filled with isobutane propellant to 9 wt % based upon the combined weight of composition and propellant.

TABLE 1

| INCI NAME | Example 1 | Example 2 | Example 3 | Example 4 | Example 5 | Example 6 |
|---|---|---|---|---|---|---|
| ISOPROPYL MYRISTATE | 32.90 | 32.90 | 32.90 | 32.90 | 32.90 | |
| AVOCADO OIL | | 47.73 | | | | |
| GRAPE SEED OIL | | | 47.73 | | | |
| APRICOT OIL | 47.7295 | | | 47.73 | 47.73 | 81.90 |
| PROPELLANT | 9.00 | 9.00 | 9.00 | 9.00 | 9.00 | 9.00 |
| OTHER INGREDIENTS (e.g., FRAGRANCE AND PRESERVATIVES) | 0.82 | 0.82 | 0.82 | 0.82 | 0.82 | |
| POLYGLYCERYL-10 TRILAURATE | | | | | 9.10 | |
| POLYGLYCERYL-2 LAURATE | 9.10 | 9.10 | 9.10 | | | |
| POLYGLYCERYL-10 DIOLEATE | | | | 9.10 | | 9.10 |

Table 2 shows various composition having a composition having varied oil and surfactants. The compositions were formed using the same process as Examples 1-6.

TABLE 2

| INCI NAME | Example 5 | Example 1 | Example 6 |
|---|---|---|---|
| ISOPROPYL MYRISTATE | 32.90 | 32.90 | |
| PRUNUS ARMENIACA (APRICOT) KERNEL OIL | 47.73 | 47.73 | 81.90 |
| PROPELLANT | 9.00 | 9.00 | 9.00 |
| OTHER INGREDIENTS (e.g., FRAGRANCE AND PRESERVATIVES) | 1.28 | 1.28 | |
| POLYGLYCERYL-10 TRILAURATE | 9.10 | | |
| POLYGLYCERYL-2 LAURATE | | 9.10 | |
| POLYGLYCERYL-10 DIOLEATE | | | 9.10 |
| Stable Foam | Yes | Yes | Yes |
| Water Rinsability | Yes | Yes | Yes |

Table 3 shows various composition having a composition varied triglyceride oil and polyglyceryl surfactants. The compositions were formed using the same process as Examples 1-6.

TABLE 3

| INCI NAME | Example 7 | Example 8 | Example 9 | Example 10 (comparative) |
|---|---|---|---|---|
| Isopropyl Myristate | 19.79 | 33.67 | 33.67 | 33.67 |
| Mineral Oil | | | | 48.23 |
| Sunflower Seed Oil | | 48.23 | | |
| Apricot Oil | 47.73 | | | |
| Olive Oil | | | 48.23 | |
| Polyglyceryl-10 Dioleate | 22.75 | | | |
| Isobutane | 9.00 | 9.00 | 9.00 | 9.00 |
| Polyglyceryl-10 Isostearate | | | 9.1 | |
| Polyglyceryl-10 Dioleate | | 8.645 | | 9.1 |
| OTHER INGREDIENTS (e.g., FRAGRANCE AND PRESERVATIVES) | 0.568 | 0.460 | | 0.004 |
| Stable Foam | Yes | Yes | Yes | No |
| Water Rinsability | Yes | Yes | Yes | Yes |

Table 4 illustrates a comparison of foamability based upon a variable polyglyceryl surfactant (concentration of polyglyceryl surfactant used was 9%, a tryiglyceride-based oil, apricot oil, was used at 48%, 9% propellant, and QS ~33% isopropyl myristate).

TABLE 4

| Name | HLB | Initial Foam (stiffness, t = 0 s) | Foam Integrity (stability, t = 30 s) | Comments |
|---|---|---|---|---|
| polyglyceryl-2 triisostearate | 3 | X | X | no foam, no integrity |
| polyglyceryl-4 isostearate | 5 | X | X | no foam, no integrity |
| polyglyceryl-3 diisostearate | 5 | ○ | X | slight foam, poor integrity |
| polyglyceryl-3 beeswax | 5 | X | X | no foam, no integrity |
| Polyglyceryl-2 oleate | 7.5 | X | X | no foam, no integrity |
| Polyglyceryl-2 laurate | 8.5 | ○ | ○ | good foam, acceptable stability |
| polyglyceryl-10 trilaurate | 10.4 | ○ | ○ | good foam and stability |
| Polyglyceryl-5 Laurate | 10.9 | ○ | ○ | acceptable foam and stability |
| polyglyceryl-10 dioleate | 11 | ○ | ○ | good foam and stability |
| polyglyceryl-6 dicaprate | 11 | ○ | ○ | acceptable foam and stability |
| polyglyceryl-10 dioleate | 11.9 | ○ | ○ | great foam and stability |
| polyglyceryl-10 isostearate | 12 | ○ | ○ | good foam and stability |
| polyglyceryl-4 caprate | 14 | X | X | no foam, no integrity |
| polyglyceryl-10 laurate | 17.1 | X | X | no foam, no integrity |

As shown above, the foam for the above compositions was evaluated aesthetically initially after formation of the foam (at t=0 s) and at 30 seconds (t=30 s). The ratings were rated on a scale of 0-5, wherein ratings greater than 2 were considered a good foam structure. An "X" indicates a lack for foam stability and "O" indicates that there was good foam structure.

Table 5 illustrates a comparison of oils utilizing the polyglyceryl fatty acid ester surfactant, according to the present invention, with a variable composition of oil (oil percentage used was 48% unless otherwise noted), 9% polyglyceryl fatty acid ester surfactant, 9% isobutane propellant, and QS ~33% with isopropyl myristate). Comparison of oils indicated that triglyceride-based oils were able to produce good and stable foams, while other oils, such as mineral oil or high levels of isopropyl myristate, failed to form a stable foam.

TABLE 5

| Name | Initial Foam (stiffness, t = 0 s) | Foam Integrity (stability, t = 30 s) | Description |
| --- | --- | --- | --- |
| Grapeseed Oil | O | O | dense foam, good stability |
| Walnut Oil | O | O | dense foam, good stability |
| Sunflower Oil | O | O | dense foam, good stability |
| Corn oil Oil | O | O | dense foam, good stability |
| Apricot Oil | O | O | dense foam, good stability |
| Camelia Oil | O | O | dense foam, good stability |
| Olive Oil | O | O | dense foam, good stability |
| Avocado Oil | O | O | dense foam, good stability |
| Oleic Acid | X | X | loose foam, no stability |
| 0% triglyceride oil, Isopropyl Myristate + QS = 81% | X | X | loose foam, no stability |
| Mineral Oil | X | X | loose foam, no stability |
| Apricot Oil (24%), Isopropyl Myristate (54% including QS) | X | X | loose foam, no stability |

As shown above, the foam for the above compositions was evaluated aesthetically initially after formation of the foam (at t=0 s) and at 30 seconds (t=30 s). An "X" indicates a failure of the foam and "O" indicates that there was good foam structure.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An aerosol oil foam composition comprising:
   (a) 35% to 60% by weight, based on the weight of the composition, of at least one triglyceride-based oil;
   (b) 8% to 25% by weight, based on the weight of the composition, of at least one polyglyceryl fatty acid ester surfactant selected from the group consisting of polyglyceryl-5 laurate, polyglyceryl-10 dioleate, polyglyceryl-6 dicaprate, polyglyceryl-10 isostearate, and combinations thereof, and having a hydrophile-lipophile balance of between about 8 and about 13; and
   (c) 1% to 15% by weight, based on the weight of the composition, of a propellant;
   wherein the aerosol oil foam composition is a stable foam that is water rinsable.

2. The aerosol oil foam composition of claim 1, wherein the triglyceride-based oil is selected from the group consisting of heptanoic or octanoic acid triglycerides, wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppyseed oil, pumpkin oil, marrow oil, blackcurrant oil, evening primrose oil, millet oil, barley oil, walnut oil, *quinoa* oil, rye oil, safflower oil, candlenut oil, camelia oil, passionflower oil, musk rose oil, shea butter, caprylic/capric acid triglycerides and combinations thereof.

3. The aerosol oil foam composition of claim 1, wherein the polyglyceryl fatty acid ester surfactant consists of polyglyceryl-10 dioleate.

4. The aerosol oil foam composition of claim 1, wherein the composition is waterless.

5. The aerosol oil foam composition of claim 1, wherein the composition is devoid of petroleum-based oil.

6. The aerosol oil foam composition of claim 1, wherein the composition is devoid of UV filters.

7. An aerosol oil-containing foamable composition containing:
   (a) 35% to 60% by weight, based on the weight of the composition, of at least one triglyceride-based oil;
   (b) at least one polyglyceryl fatty acid ester surfactant selected from the group consisting of polyglyceryl-5 laurate, polyglyceryl-10 dioleate, polyglyceryl-6 dicaprate, polyglyceryl-10 isostearate, and combinations thereof, wherein the polyglyceryl fatty acid ester surfactant is present in the composition in an amount of from 8% to 25% by weight, based on the weight of the composition, and wherein the polyglyceryl fatty acid ester surfactant has a hydrophile-lipophile balance of between about 8 and about 13; and
   (c) 1% to 15% by weight, based on the weight of the composition, of a propellant,
   wherein the aerosol oil-containing foamable composition forms a stable foam that is water rinsable.

8. The aerosol oil-containing foamable composition of claim 7, wherein the composition is devoid of petroleum-based oil.

9. The aerosol oil-containing foamable composition of claim 7, wherein the composition is devoid of UV filters.

10. The aerosol oil-containing foamable composition of claim 7, wherein the composition is waterless.

11. The aerosol oil-containing foamable composition of claim 7, wherein the triglyceride-based oil is selected from the group consisting of heptanoic or octanoic acid triglycerides, wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppyseed oil, pumpkin oil, marrow oil, blackcurrant oil, evening primrose oil, millet oil, barley oil, walnut oil, quinoa oil, rye oil, safflower oil, candlenut oil, camelia oil, passionflower oil, musk rose oil, shea butter, caprylic/capric acid triglycerides and combinations thereof.

12. The aerosol oil-containing foamable composition of claim 7, wherein the polyglyceryl fatty acid ester surfactant is polyglyceryl-10 isostearate.

13. The aerosol oil-containing foamable composition of claim 7, wherein the polyglyceryl fatty acid ester surfactant is polyglyceryl-6 dicaprate.

14. The aerosol oil-containing foamable composition of claim 7, wherein the polyglyceryl fatty acid ester surfactant is polyglyceryl-5 laurate.

15. The aerosol oil-containing foamable composition of claim 7, wherein the polyglyceryl fatty acid ester surfactant is polyglyceryl-10 dioleate.

16. The aerosol oil-containing foamable composition of claim 11, wherein the triglyceride-based oil is selected from the group consisting of grapeseed oil, apricot oil, walnut oil, and combinations thereof.

17. The aerosol oil-containing foamable composition of claim 7, wherein the propellant is present in the composition in an amount of 1% to 10% by weight, based on the weight of the composition.

18. The aerosol oil-containing foamable composition of claim 7, further comprising isopropyl myristate.

19. The aerosol oil-containing foamable composition of claim 18, wherein the isopropyl myristate and triglyceride oil are present in the composition at a ratio of about 1:1.45 to about 1:2.41.

20. The aerosol oil-containing foamable composition of claim 7, wherein the at least one triglyceride-based oil is present in the composition in an amount of 50% to 60% by weight, based on the weight of the composition.

21. An aerosol oil foam composition comprising:
(a) 50% to 60% by weight, based on the weight of the composition, of at least one triglyceride-based oil selected from the group consisting of grapeseed oil, apricot oil, walnut oil, and combinations thereof;
(b) 8% to 25% by weight, based on the weight of the composition, of at least one polyglyceryl fatty acid ester surfactant selected from the group consisting of polyglyceryl-5 laurate, polyglyceryl-10 dioleate, polyglyceryl-6 dicaprate, polyglyceryl-10 isostearate, and combinations thereof, and having a hydrophile-lipophile balance of between about 8 and about 13; and
(c) 1% to 15% by weight, based on the weight of the composition, of a propellant wherein the aerosol oil foam composition is a stable foam that is water rinsable.

* * * * *